United States Patent [19]

Robbins et al.

[11] Patent Number: 5,476,982
[45] Date of Patent: Dec. 19, 1995

[54] CATALYST FOR DEHYDROGENATION OF PARAFFINS

[75] Inventors: John L. Robbins, Stockton; Elise Marucchi-Soos, Warren; Jack W. Johnson, Clinton; John F. Brody, Bound Brook, all of N.J.

[73] Assignee: Exxon Research & Engineering Co., Florham Park, N.J.

[21] Appl. No.: 259,717

[22] Filed: Jun. 14, 1994

Related U.S. Application Data

[62] Division of Ser. No. 28,442, Mar. 9, 1993, Pat. No. 5,346,871.

[51] Int. Cl.$^6$ .................................................... C07C 5/333
[52] U.S. Cl. ........................... 585/660; 585/629; 585/661
[58] Field of Search ................................ 585/660, 661, 585/629

[56] References Cited

U.S. PATENT DOCUMENTS

| | | |
|---|---|---|
| 2,498,709 | 2/1950 | Roberts et al. . |
| 2,906,713 | 9/1959 | Hunter et al. . |
| 3,235,512 | 2/1966 | Koepernik . |
| 3,766,058 | 10/1973 | Hensley, Jr. . |
| 3,790,504 | 2/1974 | Duhaut . |
| 3,793,232 | 2/1974 | Duhaut et al. . |
| 3,821,323 | 6/1974 | Schulze et al. . |
| 3,849,296 | 11/1974 | Hensley, Jr. . |
| 3,904,554 | 9/1975 | Dicks . |
| 4,088,607 | 5/1978 | Weidenbach et al. . |
| 4,141,817 | 2/1979 | McVicker et al. . |
| 4,220,559 | 9/1980 | Polinski . |
| 4,280,930 | 7/1981 | Antos . |
| 4,374,046 | 2/1983 | Antos . |
| 4,458,098 | 7/1984 | Antos . |
| 4,510,257 | 4/1985 | Lewis et al. . |
| 4,822,699 | 4/1989 | Wan . |
| 4,962,266 | 10/1990 | Shum . |
| 5,346,871 | 9/1994 | Robbins et al. ..................... 502/61 |

FOREIGN PATENT DOCUMENTS

| | | |
|---|---|---|
| 0351067 | 1/1990 | European Pat. Off. . |
| 0090442 | 10/1993 | European Pat. Off. . |

*Primary Examiner*—Asok Pal
*Attorney, Agent, or Firm*—Estelle C. Bakun

[57] ABSTRACT

The present invention is directed to a novel catalyst composition and its use in the dehydrogenation of paraffins to olefins. The catalyst comprises an alloy of a Group VIII noble metal and a metal selected from the group consisting of zinc and gallium on a support selected from the group consisting of silica, zinc oxide modified silica and zinc oxide modified silica-pillared clays when said alloy is a zinc alloy, and silica, gallium oxide modified silica and gallium oxide modified silica-pillared clays when said alloy is a gallium alloy. The instant catalyst is an active and selective catalyst for the catalytic dehydrogenation of paraffins to olefins, especially gaseous paraffins, having the added benefit of retaining high activity and selectivity even following repeated regeneration by calcination in oxygen containing gas at temperatures of 450° C. to 650° C., preferably 450° C. to 500° C.

5 Claims, 3 Drawing Sheets

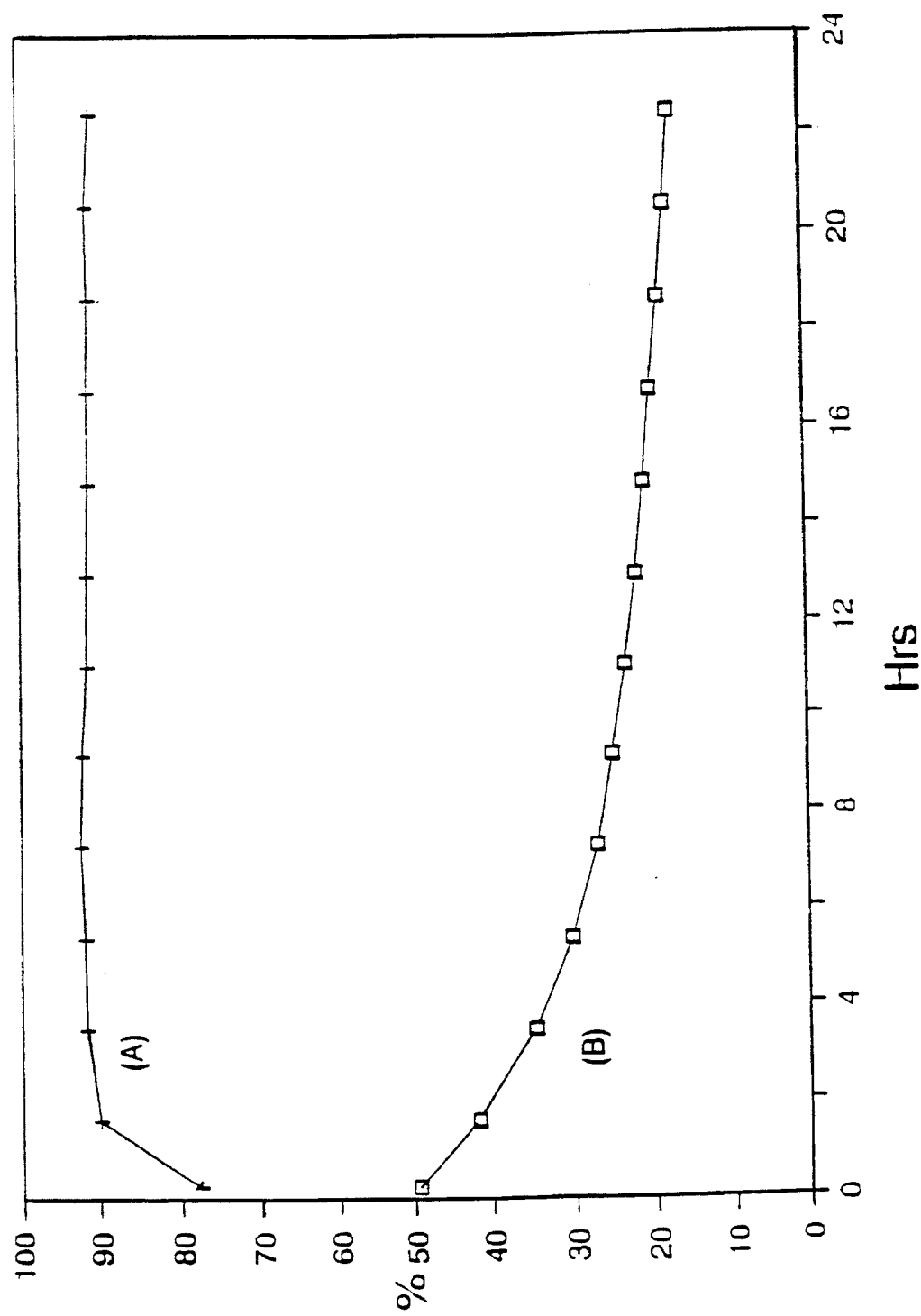

CATALYST FOR DEHYDROGENATION OF PARAFFINS

This is a division of application Ser. No. 028,442, filed Mar. 9, 1993, now U.S. Pat. No. 5,346,871.

BACKGROUND

The present invention is directed to a new catalyst composition for the dehydrogenation of paraffins, especially gaseous paraffins, e.g., ethane, pentane, butane, isobutane, and isopentane, to their respective olefin derivatives. Preferably, mono-olefins will be produced. The catalyst can also be used for the hydrogenation of olefins to paraffins or the dehydrogenation of mono-olefins to di-olefins. The mono-olefins produced have high value as precursors to fuels, chemicals, and polymers. Due to equilibrium limitations, these selective paraffin dehydrogenations reactions are typically carried out at a high, but narrow temperature range, e.g., up to 650° C. for isobutane dehydrogenation to isobutene, to maximize the olefin yield and minimize yields of undesired products such as alkynes, diolefins, and cracking products (lower molecular weight alkane olefin mixtures). Useful catalysts must exhibit high activity and selectivity for the desired dehydrogenation process and a minimal rate of deactivation. Furthermore, the coke formed in this high temperature process is very refractory and such coke formation may lead to deactivation. Complete coke removal can require combustion in $O_2$ containing gas at temperatures greater than 600° C. Desirable catalysts, therefore, must retain high paraffin dehydrogenation activity following high temperature regeneration in $O_2$ containing streams.

SUMMARY

The present invention is directed to a novel catalyst composition and its use in the dehydrogenation of paraffins to olefins. The catalyst comprises an alloy of a Group VIII noble metal and a metal selected from the group consisting of zinc and gallium on a support selected from the group consisting of silica, zinc oxide modified silica and zinc oxide modified silica-pillared clays when said alloy is a zinc alloy, and silica, gallium oxide modified silica and gallium oxide modified silica-pillared clays when said alloy is a gallium alloy. The instant catalyst is an active and selective catalyst for the catalytic dehydrogenation of paraffins to olefins, especially gaseous paraffins, having the added benefit of retaining high activity and selectivity even following repeated regeneration by calcination in oxygen containing gas at temperatures of 450° C. to 650° C., preferably 450° C. to 500° C.

Applicants' catalyst additionally maintains its high activity and selectivity for extended periods of time (at least five days) compared with commercially available prior art catalysts such as chromia-alumina and modified platinum-alumina catalysts which lose their activity and selectivity within 7 hours thereby requiring frequent regeneration.

BRIEF DESCRIPTION OF THE FIGURES

FIG. 3 illustrates the selectivity to isobutene (line A) and conversion of isobutane (line B) of the present invention platinum-zinc alloy on zinc oxide modified silica-pillared sodium tetrasilicic mica when used in the dehydrogenation of neat isobutane.

DETAILED DESCRIPTION OF THE INVENTION

Figure 1B:
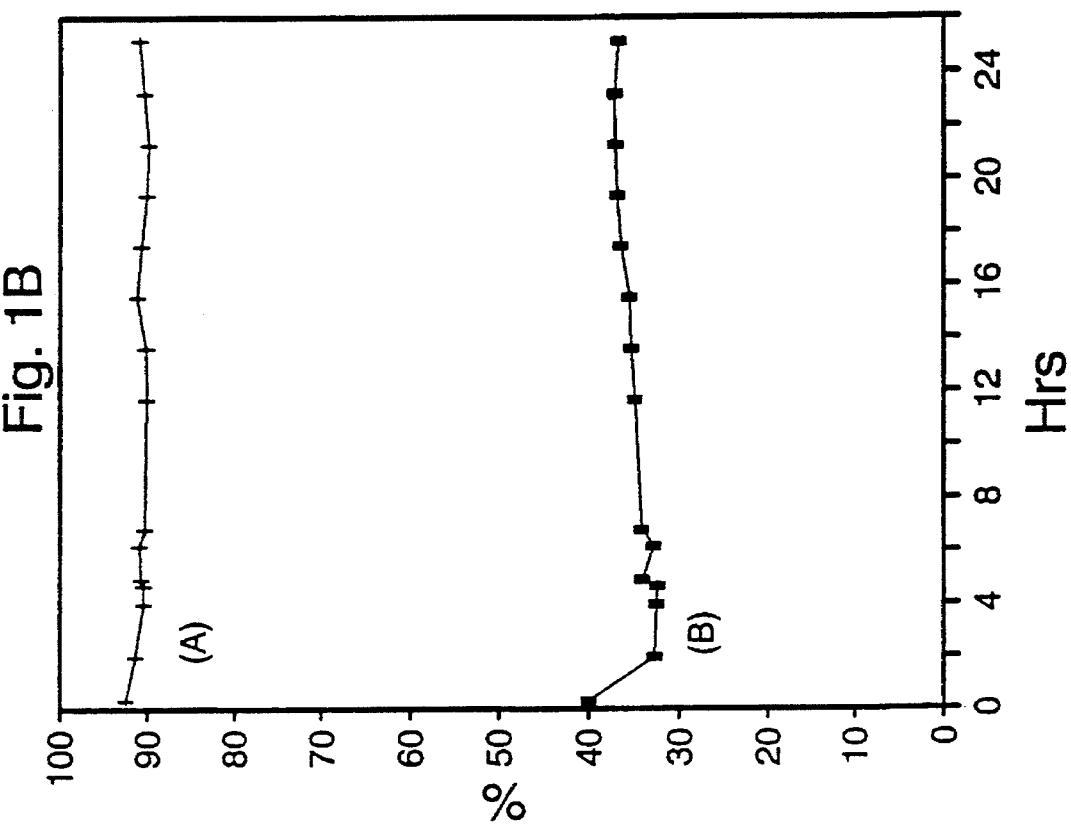
FIG. 1B illustrates the activity (line B) and selectivity (line A) of the same catalyst, following a high temperature (650° C.) regeneration in oxygen, for isobutane dehydrogenation over a 2 day period. The regenerability, as well as the maintenance of activity and selectivity of the catalyst, can readily be seen from comparison of FIGS. 1A and 1B.

The present invention catalysts are prepared by impregnating a silica or silica-pillared clay with an aqueous solution of a zinc salt or gallium salt, which upon calcination is converted to zinc oxide or gallium oxide, respectively. The amount of zinc oxide or gallium oxide to be impregnated ranges from about 0.2 wt % to about 25 wt %, preferably about 0.2 wt % to about 1.5 wt %. Typically the zinc oxide will be added to the support in the form of a salt, e.g., $Zn(NO_3)_2 \cdot 6H_2O$, zinc acetate, zinc halides, zinc formates, zinc oxalates, zinc acetylacetonates, or any other zinc salt easily converted to zinc oxide as by calcining. The gallium oxide will likewise be added to the support in the form of a salt, e.g., gallium nitrate, gallium acetate, gallium halides, gallium formates, gallium oxalates, gallium acetylacetonates, or any other gallium salt easily converted to gallium oxide as by calcining. The impregnation is accomplished via the incipient wetness technique, however, other suitable techniques known to those skilled in the art are also suitable. Zinc or gallium metal may be evaporated onto the support and exposed to air to convert it to the oxide. Organometallic zinc or gallium precursors may also be used and converted to the oxide in the presence of $H_2O$ or $O_2$. Such methods are well known to those skilled in the art. The impregnated support is then dried followed by calcination. The drying is conducted at about 100° to about 150° C. for about 12 hours, while the calcination is conducted at about 200° C. to about 500° C. for between about 6 and about 24 hours. Calcination converts the hydrated salt to the oxide. Zinc oxide is the preferred oxide contemplated by this invention.

A metal selected from the group consisting of Group VIII noble metal(s) is then impregnated onto the zinc or gallium oxide modified silica support to provide hydrogenation-dehydrogenation functions, preferably platinum is employed. The Group VIII noble metal will be present on the catalyst in an amount from about 0.01 to about 10 wt % calculated on an elemental basis of the final catalyst composition. Preferably, the catalyst will contain from about 0.01 to about 2 wt % noble metal, most preferably about 0.1 to 1 wt % noble metal. Preferably, the noble metal will be platinum.

The metal(s) can be incorporated onto the oxide modified support via the incipient wetness, or other suitable techniques known to those skilled in the art. An absorption technique from a dilute or concentrated solution, with subsequent filtration or evaporation to effect uptake of the metallic component, may also be used. The solution used in impregnating the modified support can be, e.g., a salt or acid solution having the respective Group VIII metal(s) dissolved therein. For example, chloroplatinic acid, hexachloroplatinic acid, tetrachloroplatinous acid, etc. may be used. The impregnation can be carried out under a variety of conditions known to those skilled in the art, including ambient and elevated temperatures, and atmospheric, subatmospheric, and superatmospheric conditions.

Alternatively, the catalyst can be coimpregnated with the zinc or gallium and Group VIII noble metal components.

Alternatively, platinum and zinc or platinum and gallium can be deposited onto a silica or silica-pillared clay support by well known vacuum deposition techniques and the subsequent reduction step as performed on the gallium or zinc oxide modified silica carried out.

The catalyst, after sequential or coimpregnation of the Group VIII noble metal is calcined at a temperature from 200° C. to 650° C., preferably from about 200° C. to about 450° C., in the presence of oxygen, or in an air stream, or in the presence of a mixture of oxygen and an inert gas. This calcination is conducted for periods ranging from about 1 to 24 hours in either flowing or static gases.

The Group VIII noble metal and zinc or gallium alloy is then formed by reducing the catalyst in a hydrogen atmosphere at a temperature and for a time sufficient to reduce the zinc or gallium oxide to zinc or gallium metal, respectively, and to form the alloy. The temperature can range from about 450° C. to 650° C. and the time from about 2 to 24 hours. The formation of the alloy by reduction can be performed prior to the use of the catalyst or in situ during the dehydrogenation reaction. The atomic ratio of Zn/Pt or Ga/Pt in the alloy will be greater than 0.05 but less than 1. The alloy will contain between 5 and 100 atoms of zinc or gallium per 100 atoms of platinum in the alloy, preferably 25 to 100 and most preferably 75 to 100.

The supports of the present invention are silica, silica-pillared clays, zinc oxide modified silica, gallium oxide modified silica, zinc oxide modified silica-pillared clays and gallium oxide modified silica-pillared clays with zinc oxide modified silica being preferred. Such supports are commercially obtainable or easily prepared by techniques known to those skilled in the art.

New preferred silica-pillared clays which may be utilized as supports for the present invention are silica-pillared micas. The method of producing silica-pillared micas comprises:

(a) contacting a fluoromica having layers therein with a material selected from the group consisting of organosilicon oligomer precursors and organosilicon oligomers for a time and at a temperature sufficient to allow said material to intercalate between said layers of said fluoromica;

(b) calcining said fluoromica having said material diffused therein for a time and at a temperature sufficient to decompose said material into a silica pillar and to form an intermediate pillared clay product;

(c) washing said calcined intermediate pillared clay product;

(d) recalcining said washed and calcined intermediate pillared clay product for a time and at a temperature sufficient to form a silica-pillared clay.

The new silica-pillared mica prepared from sodium tetrasilicic fluoromica in accordance with the above procedure has a silica content of at least about 30 wt % as Si; a BET surface area of more than 50 m²/g, preferably between 200 and 400 m²/g; and an average layer repeat distance measured by X-ray diffraction of between 16 and 20 Angstroms. Decompose as used herein means that the pillaring material is wholly or partially converted into silica.

The silica-pillared micas are prepared from synthetic fluoromicas such as sodium tetrasilicic mica (NaTSM) and synthetic taeniolite. Micas are formed of layers that may be visualized as sandwiches comprising two outer sheets of silicon oxide tetrahedra and an inner sheet of aluminum octahedra (i.e. 2:1 layered clay). These micas can be represented by the general formula:

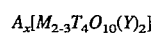

where M designates the octahedral cation, T designates the tetrahedral cation, A designates the exchangeable interlayer cations, O is less than or equal to X which is less than or equal to one, and Y is hydroxy (OH) or fluorine(F) either singly or in combination. The T ion is commonly $Si^{+4}$, $Al^{+3}$, or $Fe^{+3}$, but could also include several other four-coordinate ions, e.g., $P^{+5}$, $B^{+3}$, $Ga^{+3}$, $Cr^{+3}$, $Ge^{+4}$, $Be^{+2}$, etc. $Si^{+4}$ is preferred in this invention. The hexacoordinate M ion is typically $Al^{+}$ or $Mg^{+2}$, but could also include many other possible hexacoordinate ions, e.g., $Fe^{+3}$, $Fe^{+2}$, $Ni^{+2}$, $Co^{+2}$, $Li^{+}$, $Cr^{+3}$, $V^{+2}$, etc. $Mg^{+2}$ is preferred in this invention, and X is preferred to approximately equal one (0.7–1).

Synthetic fluoromicas such as sodium tetrasilicic fluoromica ($Na[Mg_{2.5}Si_4O_{10}F_2]$) and lithium taeniolite ($Li[(Mg_2Li)Si_4O_{10}F_2]$) undergo swelling in water and other suitable polar solvents such as ketones like acetone, methylethylketone, etc.; sulfoxides such as dimethylsulfoxide; formamides, such as dimethyl formamide and N-methyl formamide, and the like. Even though fluoromicas such as these exhibit high layer charge densities, with X in the above general formula approaching 1, they are capable of undergoing pillaring reactions with large polynuclear cations, for example, $Al_{13}O_4(OH)_{24}(H_2O)_{12}^{+7}$, $Zr_4(OH)_8(H_2O)_{16}^{+8}$, and the like. The resulting pillared tetrasilicic micas exhibit good thermal stability, increased surface area and are good sorbents and supports for catalytic reactions. See for example European Patent application 0240359 A2 to Johnson.

The process of producing the silica-pillared tetrasilicic micas begins by introducing an organosilicon oligomer which will give rise to a three dimensional supporting silica structure between the layers of the fluoromica. The mica is contacted with water or another polar solvent followed by addition of an organosilicon oligomer precursor or an organosilicon oligomer itself. Alternatively, solid mica may be added to a solution of an organosilicon oligomer precursor or a solution of an organosilicon oligomer itself. The mixture is then stirred and allowed to react. When an organosilicon oligomer precursor is utilized, it undergoes hydrolysis, in situ, to form the organosilicon oligomer which ultimately provides the pillars of the final pillared clay. Hence, the organosilicon oligomer can be referred to as the pillaring agent. Such in situ formation of the organosilicon oligomer from its precursor may occur prior to the precursor intercalating between the mica layers, or the precursor may first intercalate and then form the oligomer. Intercalate is a term of art which indicates the insertion of a material between the layers of a clay substrate. The temperature of reaction will depend on the organosilicon oligomer precursor or organosilicon oligomer selected and is readily determinable by one skilled in the art.

The organosilicon oligomer is preferably prepared in situ by reacting, in solution, its precursor with the clay to be pillared. Frequently, the pH of the solution will be adjusted to provide for optimum intercalation. For example, when the pillaring agent or its precursor contains a positively charged group, the pH should be adjusted above 5 to minimize ion exchange of hydrogen ions in preference to the pillaring agent.

The precursor forming the organosilicon oligomer in situ or the organosilicon oligomer itself is contacted, in solution, with the clay selected, for a time and at a temperature sufficient to allow for intercalation. The precursor may be converted (hydrolyzed) into the organosilicon oligomer prior to intercalation, or it may intercalate prior to converting into the oligomer. NMR results show that the precursor is only partially hydrolyzed prior to subsequent calcination. The contacting can be performed at temperatures ranging from the freezing point to the boiling point of the solvent being utilized, or from the freezing point to the boiling point of the organosilicon oligomer or its precursor when they are in liquid form and acting as the solvent. For example, when 2-(2-trichlorosilylethyl)pyridine is used as the organosilicon oligomer precursor, the pH of solution is adjusted to above 5 and the mixture of mica and organosilicon oligomer precursor allowed to react at room temperature. When aminopropyltriethoxysilane, $NH_2(CH_2)_3Si(OEt)_3$, is used as the organosilicon oligomer precursor, the pH of the precursor solution is about 10 to 11 and no pH adjustment is necessary. However, the mica and precursor solution is refluxed since alkoxysilanes are less reactive towards hydrolysis than chlorosilanes. Temperatures higher than the boiling points of the solution or the organosilicon oligomer or its precursor may be utilized if adequate pressure containment is provided. Typically, the temperature should not exceed 200° C. above the boiling point. Reaction temperatures are readily determinable by one skilled in the art based on the particular organosilicon oligomer or organosilicon oligomer precursor chosen.

Contacting time can be anywhere from at least about 1 minute to about 1 month, preferably about 1 minute to 1 week, most preferably, about 1 to about 24 hours. The higher the contacting temperature the shorter the contacting time necessary. Such contacting times are readily determinable by one skilled in the art. The resulting material is then separated by any conventional means, washed and dried.

The organosilicon oligomers may be prepared in situ by hydrolysis of an organosilicon oligomer precursor by contacting such precursor in solution with the fluoromica to be pillared. The pillaring agent used to prepare the pillared clays of the present invention is an organosilicon oligomer and may be prepared according to the procedure set forth in U.S. Pat. No. 4,510,257 to Lewis et al. herein, incorporated by reference and referred to as oligosilsesquioxanes and their homo derivatives.

The basic three dimensional silicate structure which makes up the silica pillars and the silica pillar precursors are described in the article by Voronkov et al, "Polyhedral Oligsilsesquioxanes and their Homo Derivatives," Topics in Current Chemistry, 102, pp 199–236, Springer-Verlag, 1982. These three dimensional silicate structures are known as polyhedral oligosilsesquioxanes. They are composed of a polyhedral silicon-oxygen skeleton which bears organic substituents attached to the silicon atoms. The molecules of these compounds have the general formula $(XSiO_{1.5})_n$ where n is an even number greater than or equal to 4, and X is organyl, lower alkyls, such as methyl, ethyl, propyl, butyl, hexyl, heptyl, etc; vinyl, allyl, benzyl, 2-methyl benzyl, 4-methyl benzyl, nitrobenzyl, etc., triethylammonium, aminopropyl, 2-pyridolethyl, etc. and the X may be the same or a mixture of the different substituents. These compounds may be considered as the products of complete hydrolytic condensation of the corresponding trifunctional monomers, $XSiY_3$ with Y=halogen, OH, OR, OCOR, etc.

A minor structural variation of the polyhedral silsesquioxanes are the homosilsesquioxanes. They differ from the above described oligosilsesquioxanes in that the Si-O bond of the latter is inserted by a XX'SiO group which is a homologous link in linear and cyclic oligo- and polysiloxanes. Homooligosilsesquioxanes are described by the general formula $(XSiO_{1.5})_n(OSiX_2)_m$, wherein m and n are integers and X is described as above. These compounds are the by-products of the synthesis of oligosilsesquioxanes and are usually found in minor amounts. Because of the close similarity in structure between the oligosilsesquioxanes and their homo derivatives, the term oligosilsesquioxane when used herein will include the polyhedral oligosilsesquioxanes as well as their homo derivatives. The pillar material can thus contain a mixture of polyhedral oligosilsesquioxanes and their homo derivatives.

The pillar materials used to prepare the silica-pillared micas contain one or more compounds having the general formula $(ZSiO_{1.5})_n(OSiZ_2)_m$ where m and n are zero or an integer and m+n does not equal zero. In many cases, depending on preparative techniques, m will equal zero. Z is an organic moiety which serves as a coordinating and/or exchange group which allows the entire unit to be brought between the layers of the mica to be pillared. The organic moiety can be chosen such that it contains a coordinating group that is readily intercalated into the layered structure. Examples of coordinating structures include amines, amides, sulfoxides, glycols, alcohols and the like. Alternately, the organic moiety can be chosen such that it contains a cationic species that is readily exchanged into the layered structure. Examples of cationic species include ammonium ion, phosphonium ion, sulfonium ion, pyridium ion, and the like. Z may represent a single organic moiety or a mixture of organic moieties. It is however, easier to make pillared structures having identical Z's.

There are a number of routes to the synthesis of oligosilsesquioxane pillar materials. Voronkov et al. lists several procedures for the synthesis of the oligosilsesquioxane pillar materials and in general demonstrates the state of the art in the synthesis of the compounds. Illustrative, but nonexclusive reactions for forming the polyhedral silicon-oxygen skeleton of oligosilsesquioxanes are as follows: 1. Hydrolytic condensation of trifunctional monomers, $XSiY_3$ (with X=a chemically stable substituent and Y=a highly reactive substituent). 2. Condensation of Si-functional oligoorganylcyclosiloxanes, $[XYSiO]_m$ (e.g., $[C_2H_3SiHO]_{4.5}$).

3. Cocondensation of organosilicon monomers and/or oligomers of different structure and composition.

4. Thermolysis of polyorganyl silsesquioxanes.

In some cases, these reactions may be combined in order to obtain certain oligosilsesquioxanes or to increase the yield.

The preferred method of preparing the pillar materials starts with the hydrolytic condensation of the trifunctional monomers, $XSiY_3$. Hydrolytic polycondensation of trifunctional monomers of the type $XSiY_3$ leads to cross-linked three-dimensional as well as network and cissyndiotactic (ladder-type) polymers, $(XSiO_{1.5})_n$. With increasing amount of solvent, however, the corresponding condensed polycyclosiloxanes, polyhedral oligosiloxanes and their homo derivatives may be formed. The reaction rate, the degree of oligomerization and the yield of the polyhedral compounds formed strongly depend on the following factors:

1. Concentration of the initial monomer in the solution
2. Nature of solvent
3. Character of substituent X in the initial monomer
4. Nature of functional groups Y in the initial monomer
5. Type of catalyst
6. Temperature 7. Addition of water
8. Solubility of the polyhedral oligomers formed
9. pH Variations of the above factors have been studied in general and can be found in the literature, such as the aforementioned Voronkov et al. reference; otherwise, they can be determined by one skilled in the art through routine experimentation.

Oligosilsesquioxanes are formed in both polar and non-polar solvents. Illustrative, but nonlimiting examples of solvents that have been found useful include benzene, toluene, cyclohexane, hexamethylsiloxane, acetone, ethyl ether, alcohols, such as methyl, ethyl, propyl and benzyl alcohol, ketones, organic acids, their anhydrides or esters, ketones, toluene, nitrobenzene, pyridine, ethylene glycol dimethyl ether, tetrahydrofuran, acetonitrile, diglyme, methyl isobutyl ketone.

Illustrative but nonlimiting examples of the substituent X in the initial monomer $XSiY_3$ include the lower alkyls, such as methyl, ethyl, propyl, butyl, hexyl, heptyl, etc; vinyl, allyl, benzyl, 2-methylbenzyl, 4-methylbenzyl, nitrobenzyl, etc., triethylammonium, aminopropyl, 2-pyridoethyl, and mixtures thereof.

Illustrative but nonlimiting examples of the substituent Y in the initial monomer $XSiY_3$ include, hydroxyl, halo such as chloro, bromo, iodo, alkoxy such as methoxy, ethoxy, acyloxy, and mixtures thereof.

Temperatures for the hydrolytic polycondensation of the monomer $XSiY_3$ are relatively low. Temperatures will vary depending on the monomer, solvent and other reaction conditions. Reported temperatures range from below 0° C. to 160° C.

The Z moiety in the oligosilsesquioxane pillar material $(ZSiO_{1.5})_n$ will be the X moiety of the monomer $XSiY_3$, i.e., pillar material $(ZSiO_{1.5})_n$=condensation product $(XSiO_{1.5})_n$ or the X of the condensation product $(XSiO_{1.5})_n$, can be modified or replaced by a different moiety through subsequent chemical reaction on $(XSiO_{1.5})_n$. Preferably all the Z's on a pillar material will be the same. However, it is possible, through special techniques such as the hydrolytic cocondensation of 2 or more monomers with different X's, to produce pillar precursors having different Z moieties. It is postulated that the size of the moiety Z is one of the factors that can affect the pore size distribution in the final calcined product. An increase in the bulk or size of the Z-moiety is expected to increase the interpillar distance, all other variables being held constant.

Hydrolyzable pillar precursors having groups capable of bearing a positive charge, such as amino groups, pyridyl groups, or phosphonium groups, rather than neutral precursors are preferred for preparing the silica oligomers. Preferably, an organosilicon oligomer prepared from 2-(2-trichlorosilylethyl) pyridine will be used. A more preferred organosilicon oligomer precursor is aminopropyltriethoxysilane, $NH_2(CH_2)_3Si(OEt)_3$.

The dried intercalated clay is calcined at an intermediate temperature for several hours, preferably about 1 to about 24 hours. This intermediate calcination temperature is sufficient to initiate the decomposition of the organosilicon oligomer to silica that forms the pillars of the intermediate pillared clay product. Intermediate pillared clay product as used herein means the pillared clay obtained following the first calcination of the process. Intermediate calcination temperature as used herein means a calcination temperature at which the first calcination of the process is conducted, which temperature is lower than the temperature of the final calcination by about 100° C. to about 300° C.. Typically such intermediate calcination temperature will range from about 200° C. to about 600° C. Preferably, the intermediate calcination will be a staged calcination conducted at 400°–450° C. for at least about 1 hour, with lower temperatures possible throughout the remainder of the calcination step. Staged calcination means that the calcination temperature is gradually increased till the highest temperature desired is reached. The staged calcination need not be a linear increase, but can be increased for example from 200° to 400° C. and held at 400° C. followed by another increase etc. However, linear increases in temperature are effective.

After the intermediate calcination, the resultant material is washed with water or another suitable polar solvent, such as acetone, dimethyl formamide, dimethyl sulfoxide, N-methyl formamide, propylene carbonate, methanol, etc. The conditions of wash treatment must be sufficient to result in high surface area pillared mica after final calcination. When the wash step is performed with water at ambient temperature, periods of 1 to 5 days are sufficient, with 3–5 days preferred. By raising the temperature of the wash step to temperatures from 30° to 100° C., the duration of the wash step can be shortened.

After the intermediate calcination, followed by washing, the resultant material is recalcined to the second or final calcination temperature. This second calcination temperature must be sufficient to complete conversion of the organosilicon oligomer of the intermediate pillared product to a silica-pillared clay. Typically, the second calcination will be run at temperatures ranging from about 400° C. to about 800° C. Again, the calcination temperature will preferably be staged and held at about 400° C. for about 1 hour and will ultimately be increased to about 600° C. for at least about 1 hour during the calcination procedure. It is important that the intermediate, or first, calcination step be conducted at a lower temperature than the final, or second calcination step to afford a product with increased surface area. By including a washing step followed by a second calcination after calcination at an intermediate temperature, applicants have found that the surface area of the pillared clay product is increased by as much as an order of magnitude. Typically the difference between the highest temperature of the intermediate calcination and the highest temperature of the final calcination will be at least about 100° C. The final calcination is conducted for several hours, preferably about 1 to about 24 hours.

The catalyst of the present invention can be contacted with a feedstream comprising $C_2$ to $C_5$ paraffins under dehydrogenation conditions, for a time and at a temperature sufficient to produce olefins. Preferably mono-olefins will be produced. For example, during an isobutane dehydrogenation, the temperature will range from 475° C. to 650° C., preferably 575° C., P=0.1–10 atm hydrocarbon, preferably 0.5–3 atm hydrocarbon, and LHSV 0.05–6. For isopentane dehydrogenation, the temperature will be 400° C. to 525° C., preferably 450° C. to 525° C. with other conditions remaining the same. The alkanes may be cofed with $H_2$ and/or inert gas. The $H_2$:alkane or inert:alkane ratio will be about 0.1 to 3, preferably 0.1 to 0.5. Steam may be used if desired as a diluent or heat transfer agent.

The following examples illustrate the invention and are not limiting in any way.

EXAMPLE 1

Preparation of 0.8 wt % Pt on zinc oxide modified silica. Alloy prepared in situ during dehydrogenation reaction.

Shell silica spheres, commercially available, were calcined in air at 650° C. for 24 hours. An aqueous solution of zinc nitrate (146.9 g of $Zn(NO_3)_2.6H_2O$ in 180 mL $H_2O$)

was added dropwise to 160 g of calcined silica and the solid was dried in air for 18 hours at 100° C. The solid was then transferred to a quartz tube and treated in 1% $O_2$/He for 10 hours at a temperature of 250° C. The spheres were then crushed and sieved to 60/100 mesh. An aqueous solution of chloroplatinic acid was used to introduce 0.8 wt % platinum onto the ZnO-SiO$_2$ surface via the incipient wetness technique.

Preparation of 0.6 wt % Pt on silica.

Shell silica spheres were calcined in air at 650° C. for 24 hours. The spheres were then crushed and sieved to 60/100 mesh. An aqueous solution of chloroplatinic acid was used to introduce 0.6 wt % platinum onto the SiO$_2$ surface via the incipient wetness technique.

Both of the above catalysts were calcined in 3% $O_2$/He at 400° C. for 18 hours (heating rate of 1.5 ° C./min from 40° C. to 400° C.).

Catalyst Testing

The dehydrogenation of neat isobutane was studied using 0.20 g of catalyst in a fixed bed downflow microreactor with an external thermocouple. Products were analyzed with an online gas chromatograph. Catalyst activity measurements were made at atmospheric pressure and 575° C. with a feed gas hourly space velocity of 890 V/V-hr. The calcined catalysts were heated at 1.5° C./min to 575° C. in H$_2$ and held at 575° C. in H$_2$ for 1.5 hours prior to exposure to isobutane feed at 575° C.

Figure 1A:
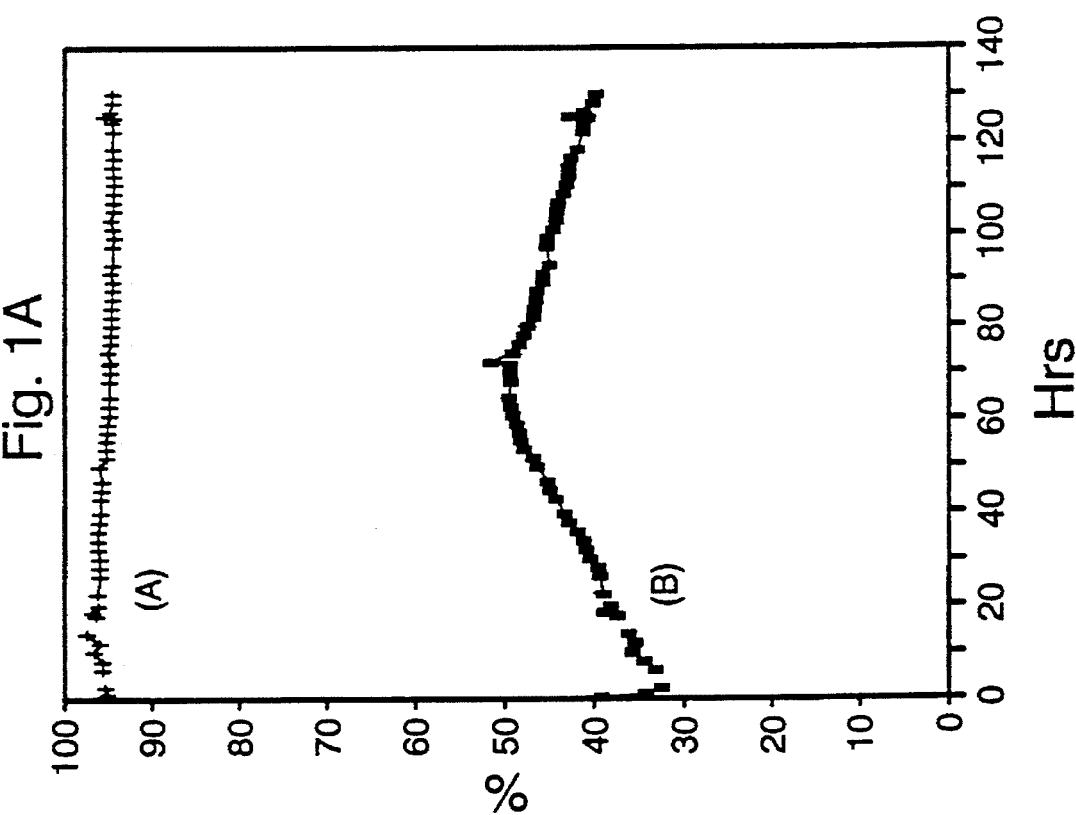
FIG. 1A illustrates the activity (line B) and selectivity (line A) of a catalyst of the instant invention in isobutane dehydrogenation over a five day period.

FIG. 1A illustrates the conversion and selectivity of Pt/ZnO-SiO$_2$ in isobutane dehydrogenation over a 5 day period. The Pt-Zn alloy was formed in situ in accordance with Example 1. Isobutane conversion ranged from 37 to 50% (average 43%) and selectivity to the desired isobutene product remained >95% throughout this period. The isobutane conversion and selectivity seen are both comparable to those reported for commercial chromia/alumina and modified platinum alumina catalysts at the same temperature and space velocity. However, most of these commercial catalysts are unable to maintain this activity/selectivity for periods greater than seven hours and thus require more frequent regeneration than the present catalyst. FIG. 1A shows the results of the present invention catalyst. Isobutene selectivity is indicated by line A and isobutane conversion by line B. The X axis indicates time in hours and the Y axis mole % isobutane conversion and selectivity.

A comparative run for the catalyst without zinc oxide modification under identical conditions of temperature, pressure, and space velocity, showed that the unmodified catalyst gave only 7% isobutane conversion with much lower (55%) selectivity to isobutene. Cracking and isomerization products comprised the balance of the carbon-containing products.

EXAMPLE 2

To test the catalysts regenerability, half of the Pt/ZnO-SiO$_2$ catalyst used in the isobutane dehydrogenation run shown in FIG. 1A was calcined in 3% $O_2$/He for 2 hours at 650° C., then reduced with H$_2$ at 575° C. for 1 hour. The catalyst was then again exposed to isobutane feed (SV:890V/V-hr) at 575° C. FIG. 1B shows the used catalyst regained its previous isobutane dehydrogenation activity and isobutene selectivity following the high temperature carbon burn or regeneration. The axes are as in FIG. 1A.

EXAMPLE 3

Davison 62 silica, commercially available, was sieved to 60/100 mesh. An aqueous solution of zinc nitrate (1.975 g Zn(NO$_3$)$_2$.6H$_2$O in 29.73 cc in H$_2$O) was added dropwise to 30 g silica, and the solid was dried in air for 18 hours at 100° C. The solid was then transferred to a quartz tube and treated in 1% $O_2$/He for 10 hours at a temperature of 250° C. An aqueous solution of chloroplatinic acid was used to introduce 0.8 wt % platinum onto the ZnO-SiO2 surface. ICP analysis showed the actual concentrations of Zn and Pt to be 1.35 and 0.768 weight percent, respectively. This catalyst was then pretreated by calcining in air at 450° C. for 16 hours, followed by reduction in hydrogen at 575° C. for 1.5 hours.

EXAMPLE 4

Figure 2:
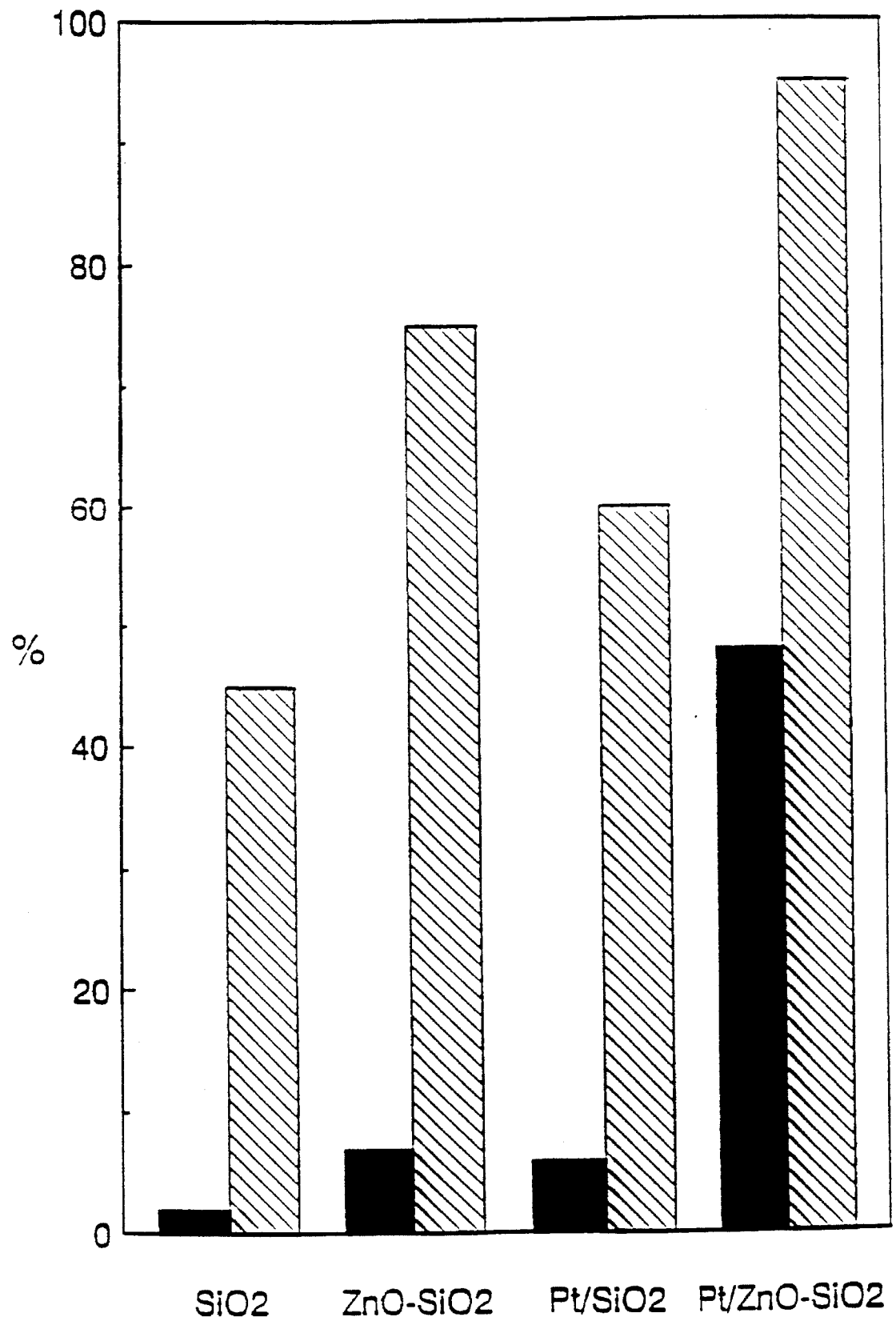
FIG. 2 illustrates the synergistic effect of the present invention catalysts. The graph shows the isobutane conversion (solid bar) and selectivity (lined bar) for a silica support ($SiO_2$), a zinc oxide modified silica support ($ZnO$-$SiO_2$), platinum on silica (Pt/$SiO_2$), and the platinum zinc alloy on zinc oxide modified silica (Pt/$ZnO$-$SiO_2$).

FIG. 2 illustrates the synergistic effect of the present invention catalyst. The graph shows the conversion and selectivity for the silica support (SiO$_2$), silica modified by zinc oxide (ZnO-SiO$_2$), platinum on silica (Pt/SiO$_2$), and the present invention catalyst having the Pt-Zn alloy formed in situ (Pt-Zn/ZnO-SiO$_2$). The zinc oxide modified silica was prepared as in Example 1 with Pt addition omitted. All other catalysts were prepared in accordance with Example 1; except for the present invention catalyst, which was prepared according to Example 3. The black bars indicate conversion and the cross hatched bars selectivity. The X axis shows the catalyst and the Y axis %. The catalysts were tested for isobutane conversion at 575° C. and GHSV=890 V/V-hr.

EXAMPLE 5

Preparation of silica-pillared tetrasilicic mica loaded with 0.5 wt. % Zn and 0.5 wt. % Pt using NH$_2$(CH$_2$)$_3$Si(OC$_2$H$_5$)$_3$ and an intermediate wash step.

500 grams of sodium tetrasilicic mica (NaTSM) obtained from Showa Sangyo Co., Ltd, were dispersed in 20 liters of deionized water by mixing five batches of 100 grams of said mica in 4 liters of water and blending each batch for 4 minutes at room temperature. Each batch of the blended mica mix was then decanted into a glass reaction vessel. The pH of the mica mix was adjusted to 5.0 as it was stirred. The mixture was allowed to settle for 1 hour at room temperature. The mica mix was then spray dried at an inlet temperature of 230°–250° C., an outlet temeprature of 120°–135° C., and a feed rate of 4–5 liters per hour.

5.00 grams of the thus purified NaTSM were added to a solution containing 12 ml of NH$_2$(CH$_2$)$_3$Si(OC$_2$H$_5$)$_3$ in 200 ml of distilled water. The mixture was refluxed with stirring for two days. The solid was separated by centrifugation and then washed five times with 1 liter portions of distilled water. The solid was dried in an oven at 120° C. and then placed in a muffle furnace where it was heated in air for 2 hours at 200° C. and then 2 hours at 400° C. The material was then stirred in 1 liter of distilled water for one day, isolated by centrifugation, stirred again in I liter of distilled water for 3 hours and isolated by centrifugation and filtration. The water-washed material was heated in air at 120° C. for 2 hours, then at 200° C. for 2 hours, then at 400° C. for 2 hours, and finally at 600° C. for 2 hours. The x-ray diffraction pattern of the product silica-pillared tetrasilicic mica (SiTSM) showed a low angle diffraction peak corresponding to a layer spacing of 17.5 A. The surface area was 250 m$^2$/g.

An aqueous solution of Zn(NO$_3$)$_2$ was used to introduce about 0.5 wt. % Zn onto the 600° C. treated SiTSM via the incipient wetness method. The Zn-treated solid was dried in air at 120° C. for 2 hours, then at 200° C. for 2 hours, and finally at 400° C. for 2 hours. An aqueous solution of H$_2$PtCl$_6$ was used to introduce about 0.5 wt. % Pt onto the Zn-treated SiTSM via the incipient wetness technique. This material was dried in air at 120° C. for 2 hours, then at 250° C. for 2 hours, and finally at 350° C. for 2 hours. The resulting material had a surface area of 222 m$^2$/g and a layer spacing of 17.3 A. Elemental analysis revealed Pt (0.48 wt.

%), Zn (0.44 wt. %), Si (30.7 wt. %), Mg (12.3 wt. %), and Na (1.09 wt. %). This powder was pelletized, then crushed and sieved to 80/100 mesh for catalyst testing.

Catalyst Testing

The dehydrogenation of neat isobutane was studied with a 0.20 gram charge of the 80/100 mesh Pt-Zn/SiTSM catalyst using the reactor system described in Example 1. Catalyst activity measurements were made at atmospheric pressure and 575° C. with a feed gas hourly space velocity of 362 V/V-hr. The catalyst was heated at 1.5° C./min to 575° C. in $H_2$ for 1.5 hours prior to exposure to isobutane feed at 575° C. FIG. 3 illustrates the conversion and selectivity of the Pt-Zn/SiTSM catalyst over a 24 hour period. Selectivity to isobutene is indicated by line A and conversion of isobutane by line B.

What is claimed is:

1. A catalytic. dehydrogenation reaction conducted under dehydrogenation conditions comprising contacting a catalyst composition with a feedstream containing $C_{2+}$ paraffins, and converting said $C_{2+}$ paraffins to olefins wherein said catalyst comprises an alloy of a Group VIII noble metal and a metal selected from the group consisting of zinc and gallium on a support selected from the group consisting of silica, silica-pillared clays, zinc oxide modified silica and zinc oxide modified silica-pillared clays when said alloy is a zinc alloy, and silica, silica-pillared clays, gallium oxide modified silica and gallium oxide modified silica-pillared clays when said alloy is a gallium alloy.

2. A catalytic dehydrogenation reaction according to claim 1 wherein said feedstream, preferably comprises $C_4$ or $C_5$ paraffins.

3. A catalytic dehydrogenation reaction according to claim 2 wherein said feedstream comprises an isobutane feedstream.

4. A catalytic dehydrogenation reaction according to claim 2 wherein said feedstream comprises an isopentane feedstream.

5. A catalytic dehydrogenation reaction according to claim 2 wherein said catalyst comprises a platinum and zinc alloy on zinc oxide modified silica.

* * * * *